(12) United States Patent
Miron

(10) Patent No.: US 12,220,499 B2
(45) Date of Patent: Feb. 11, 2025

(54) NON-RESORBABLE BONE ALLOGRAFTS AND METHOD FOR MAKING SAME

(71) Applicant: Miron Research and Development in Dentistry, LLC, Venice, FL (US)

(72) Inventor: Richard John Miron, Venice, FL (US)

(73) Assignee: Miron Research and Development in Dentistry, LLC, Venice, FL (US)

( * ) Notice: Subject to any disclaimer, the term of this patent is extended or adjusted under 35 U.S.C. 154(b) by 768 days.

(21) Appl. No.: 16/659,604

(22) Filed: Oct. 22, 2019

(65) Prior Publication Data

US 2020/0129668 A1 Apr. 30, 2020

Related U.S. Application Data

(60) Provisional application No. 62/751,298, filed on Oct. 26, 2018.

(51) Int. Cl.
| | |
|---|---|
| *A61L 27/36* | (2006.01) |
| *A61L 2/04* | (2006.01) |
| *A61L 27/38* | (2006.01) |
| *A61L 27/50* | (2006.01) |
| *A61P 19/08* | (2006.01) |

(52) U.S. Cl.
CPC .......... *A61L 27/3691* (2013.01); *A61L 2/04* (2013.01); *A61L 27/3608* (2013.01); *A61L 27/3683* (2013.01); *A61L 27/3687* (2013.01); *A61L 27/3847* (2013.01); *A61P 19/08* (2018.01); *A61L 2430/12* (2013.01)

(58) Field of Classification Search
CPC .......... A61L 27/3608; A61L 27/3683; A61L 27/3687; A61L 27/3691
See application file for complete search history.

(56) References Cited

U.S. PATENT DOCUMENTS

2014/0255489 A1* 9/2014 Shi .................. A61L 27/3608
424/549

FOREIGN PATENT DOCUMENTS

| DE | 19543110 C2 | 5/1998 |
|---|---|---|
| WO | 2004/049900 A3 | 12/2004 |

OTHER PUBLICATIONS

Malinin et al., Dentistry, 2014, vol. 4(2):199.*
Hosseinzadeh et al., Int. J. Organ Transplant. Med., 2014, vol. 5(1):23-31.*
Rana et al., Int. J. Complement. Alt. Med., 2017, 8(3): 00263.*
Malinin TI, Temple HT, Garg AK (2014) Bone Allografts in Dentistry: A Review. Dentistry 4: 199. doi:10.4172/2161-1122.1000199.

* cited by examiner

*Primary Examiner* — Xiaozhen Xie
(74) *Attorney, Agent, or Firm* — Tuggle Duggins P.A.; Blake P. Hurt; Reinier R. Smit

(57) ABSTRACT

A method for producing non-resorbable bone allografts having improved osteoconductivity and biocompatibility in regenerative dental and medical applications as compared with non-resorbable xenografts. The method comprises excising one or more bone allografts from a donor's body; freeze-drying the bone allografts; demineralizing the freeze-dried bone allografts; preserving and sterilizing the bone allografts; and thermal processing of the bone allografts at a temperature greater than about 300 degrees Celsius.

9 Claims, 1 Drawing Sheet

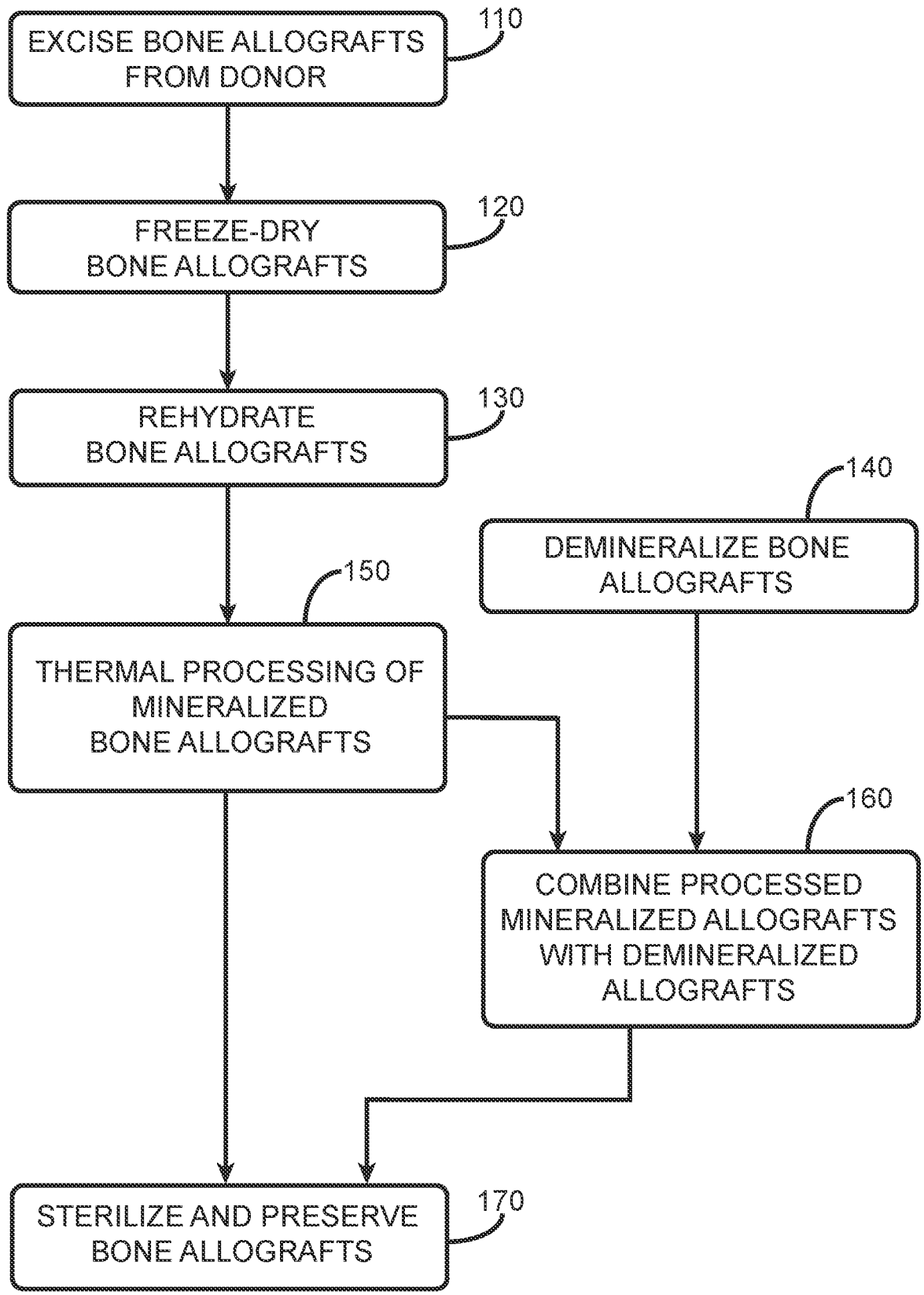

NON-RESORBABLE BONE ALLOGRAFTS AND METHOD FOR MAKING SAME

CROSS REFERENCE TO RELATED APPLICATIONS

The present application claims the benefit to U.S. Provisional Patent Application No. 62/751,298 filed on Oct. 26, 2018, which is incorporated herein by reference in its entirety.

FIELD

The present disclosure relates to the production of non-resorbable bone allografts to be used in medical and dental applications.

BACKGROUND

The use of bone grafting materials in dentistry and orthopedics has become widespread over the past two decades. The most common classification of bone grafting materials involves the following: 1) autogenous bone coming from the same individual, 2) allografts coming from human cadaver bone, 3) xenografts coming from another animal source, and 4) synthetically fabricated alloplasts.

Some bone grafting materials, such as autografts and allografts, are more osteoinductive owing to their incorporation of human growth factors that facilitate the regrowth of bone. Other bone grafting materials, such as xenografts, are generally processed differently, such as through thermal processing. As a result, many xenografts are considered non-resorbable, meaning that they prevent future resorption. Due to the wide range of uses for bone grafting materials, no single bone grafting material can fulfill each of these functions. Thus, it is often necessary to use different bone grafts for different clinical indications or even to combine two or more classes of bone graft materials to obtain a successful and predictable result.

Currently, xenografts are often used as a "non-resorbable" bone graft due to their higher temperature processing techniques. In other words, the dissolution of xenografts is typically not possible following heating due to a solubility change caused by thermal processing of hydroxyapatite. Since xenografts are derived from animal sources and are completely deproteinized following thermal processing, the xenografts are typically not as biocompatible to the human body as compared to allografts. As such, xenografts form bone less efficiently as compared with allografts. While allografts have better biocompatibility than xenografts, allografts are commonly used as a resorbable material with improved bone conducing or inducing properties. Thermal processing of allografts is not typically performed since it often results in the denaturing of growth factors and proteins within the allografts.

Often times, there is a clinical need to combine both xenografts and allografts to include the bone-inducing properties of allografts and to maintain the non-resorbable properties of xenografts. However, each product must be purchased separately and combined at a later time. In addition, xenografts are typically not as biocompatible as allografts.

Consequently, there is a need for a method to produce non-resorbable bone grafts having improved bone conducing properties and biocompatibility in regenerative dental and medical applications.

SUMMARY

What is provided is a method for producing non-resorbable bone allografts having improved osteoconductivity and biocompatibility in regenerative dental and medical applications as compared with non-resorbable xenografts.

In some embodiments, the non-resorbable allografts generated herein may be combined with various other processed allografts to include both non-resorbable and resorbable features. For example, the non-resorbable features of the allografts generated herein may be combined with osteoinductive properties of typical demineralized bone allografts.

In an embodiment, the method for making a non-resorbable bone allograft comprises excising one or more bone allografts from a donor's body; freeze-drying the bone allografts; demineralizing the freeze-dried bone allografts; preserving and sterilizing the bone allografts; and thermal processing of the bone allografts at a temperature greater than about 300 degrees Celsius.

In some embodiments, the method comprises, prior to preserving and sterilizing the bone allografts, demineralizing a second set of freeze-dried bone allografts, wherein the second set of bone allografts were not thermally processed; and combining the second set of demineralized bone allografts with the first set of thermally processed, mineralized bone allografts and/or with a third set of bone allografts, wherein the third set of bone allografts were freeze-dried but not thermally processed, and wherein the third set of bone allografts are mineralized.

BRIEF DESCRIPTION OF THE DRAWINGS

The above, as well as other advantages of the present disclosure, will become readily apparent to those skilled in the art from the following detailed description when considered in light of the accompanying drawings in which:

FIG. 1 illustrates a flow chart of an exemplary method for making a non-resorbable bone allograft.

DETAILED DESCRIPTION

It is to be understood that the invention may assume various alternative orientations and step sequences, except where expressly specified to the contrary. It is also understood that the specific devices and processes illustrated in the attached drawings, and described in the specification are simply exemplary embodiments of the inventive concepts disclosed and defined herein. Hence, specific dimensions, numbers, directions or other physical characteristics relating to the various embodiments disclosed are not to be considered as limiting, unless expressly stated otherwise.

Additionally, unless defined otherwise or apparent from context, all technical and scientific terms used herein have the same meanings commonly understood by one of ordinary skill in the art to which this disclosure belongs.

As used herein, the term "allograft" refers to a graft of tissue obtained from a donor of the same species as the recipient of the tissue graft.

As used herein, the term "non-resorbable" refers to a graft of tissue that does not resorb in the body.

As used herein, the term "osteoconductive" refers to the ability for a graft to stimulate the attachment, migration, and distribution of vascular osteogenic cells within the graft material.

As used herein, the term "osteoinductive" refers to the ability for a graft to induce bone via growth factor release and ability to form ectopic bone.

As used herein, the term "resorbable" refers to a graft of tissue that is resorbed and replaced by native host tissue bone over time.

As used herein, the term "xenograft" refers to a graft of tissue obtained from a donor of a different species than the recipient of the tissue graft.

Compositions and methods are provided for producing non-resorbable allografts having improved biocompatibility in regenerative dental and medical applications as compared with non-resorbable xenografts.

Xenografts may be deproteinized and/or demineralized under different physiochemical conditions, which selectively modulate the tissue response of a host organism. Some xenograft biomaterials undergo a chemical extraction process at a temperature of about 300 degrees Celsius to become non-resorbable. This process removes all of the organic components while maintaining a similar porosity, size, and trabecular architecture of bone. Other xenograft biomaterials undergo an extraction process at a higher heat of about 1,100 degree Celsius to become non-resorbable. This process deproteinizes the proteins found within the graft material and fuses bone crystallites together, which produces a large non-homogenous crystal morphology with decreased porosity and surface area. One of ordinary skill in the art would appreciate that the varying processes affect the physiochemical processes and biological outcomes of the xenograft biomaterials, though both may be deemed non-resorbable.

Several processes are used to allow for patient donor bone to be re-utilized as tissue allografts in a safe and convenient manner for recipients of allografts and to ensure optimal biological properties of the bone allografts are achieved.

FIG. 1 illustrates a flow chart of an exemplary method 100 for making a non-resorbable allograft material. The method 100 commences at block 110 where bone allografts are excised from a donor's body. If the donor's body had been refrigerated, the bone allografts are excised within 24 hours after death. If the donor's body was not refrigerated, the bone allografts are excised within 12 hours of death. Bone excision is performed in a clean room setting using commonly known aseptic surgical techniques.

Next, as shown at block 120, the bone allografts undergo freeze drying, which refers to the natural sublimation of water. In this block, the water is removed from the ice as vapor. As a result, the ice from a frozen biological structure disappears without melting and the water vapor is re-solidified on a colder surface. Freeze-drying the bone allografts contributes to alterations in protein configuration and/or the blocking of hydrophilic sites of proteins. These alterations in protein configuration reduce the antigenicity of freeze-dried bone.

In some examples, the freeze-dried bone allografts may be placed into freeze-dryer chambers of a condenser. The temperature of the chamber may be maintained between about −60 degrees Celsius and −70 degrees Celsius. The vacuum in the chamber is between about 10 and 20 Millitorr. The freeze-drying cycle may be maintained between about two and fourteen days. The length of the freeze-drying cycles depends on the efficiency of the chamber, the amount of material placed in the chamber, and on the different ways of measuring residual moistures.

In an alternative embodiment, instead of undergoing freeze drying as described in step 120, the allografts may be frozen to temperatures between about −15 and −20 degrees Celsius for a limited amount of time. In some examples, the bone allografts are frozen from about three months to about one year. The allografts may also undergo long-term storage at very low (cryogenic) temperatures, such as below −120 degrees Celsius. Temperatures below −120 degrees Celsius may be obtained through the use of liquefied (cryogenic) gases, such as liquid nitrogen, or through low-temperature mechanical freezers. At such temperatures, the gradual growth of ice crystals ceases entirely.

Next, as shown in block 130, the freeze-dried bone allografts are rehydrated to preserve their desired biomechanical properties. In some clinical examples, the freeze-dried bone allografts are not rehydrated. Instead, the bone particles become rehydrated by bodily fluids.

As shown in block 150, the mineralized bone allografts then undergo thermal processing at a temperature greater than about 300 degrees Celsius. In one embodiment, the allograft material undergoes thermal processing at about 1,200 degrees Celsius for about 1 hour. In another embodiment, the allograft material undergoes thermal processing at about 900 degrees at Celsius for about 4 hours. In yet another embodiment, the allograft material undergoes thermal processing at about 300 degrees Celsius for about 12 hours. One of ordinary skill in the art would appreciate that a non-resorbable allograft material may be formed through thermal processing at various temperatures and for various amounts of time.

In some embodiments, a first set of bone allografts is thermally processed, while a second set of rehydrated bone allografts is demineralized, as shown in block 140. The bone allografts may be demineralized on hydrochloric acid until the calcium content is reduced to less than 2%. Demineralization helps to more favorably induce release of bone-inducing growth factors, such as associated bone morphogenetic proteins (BMPs), which render the grafts osteoinductive. Some types of freeze-dried bone allografts, such as demineralized bone matrix (DBM) may undergo a second round of refreezing and drying. In an alternative embodiment, the freeze-dried bone allografts are still osteoinductive without being demineralized.

The thermally processed mineralized bone allografts and the demineralized bone allografts may then be combined together, as shown in block 160.

The different forms of bone allografts are then sterilized and/or preserved, as shown in block 170. In an embodiment, the bone allografts are preserved and sterilized by being immersed into chemical solutions. Some examples of sterilization and preservation techniques include irradiation and sterilization with ethylene oxide gas. Irradiating bone allografts helps prevent the transmission of infections, such as those caused by HIV. Sterilization of bone allografts with ethylene oxide helps render the bone allografts free of active bacterial, fungal, or viral infectious agents and allows them to be sold safely to the public.

In other embodiments, there are other methods for producing a non-resorbable allograft material. Since each bone allograft has its own requirements for healing, immobilization, and bone grafting, there is no universal, all-purpose bone allograft and no one method for preparing all bone allografts.

Many applications in regenerative dentistry and medicine, such as contour augmentations, sinus augmentations, etc., favor the use of non-resorbable bone grafts. The invention disclosed herein provides a new class of allografts configured as a non-resorbable material and a method for producing such allografts.

In some embodiments, the non-resorbable allografts generated herein may be combined with various other processed allografts to include both non-resorbable and resorbable features. For example, the non-resorbable features of the allografts generated herein may be combined with osteoinductive properties of typical demineralized bone allografts.

In an embodiment, the non-resorbable allograft may be combined with freeze-dried bone allografts for ridge augmentation procedures.

Examples for using the non-resorbable allografts disclosed herein are provided below. These examples are for illustrations only and in no way limit the scope of the disclosure.

EXAMPLE 1

For sinus grafting applications, allograft materials, alone, are not typically the preferred choice since their resorption over time results in limited bone volume following grafting. As a result, xenografts are typically more commonly used in these applications. However, due to the high thermal processing of the xenografts, the entire protein content of xenografts are often lost and the generated graft is limited in its osteoconductive properties. Combining non-resorbable xenografts with resorbable allografts allows for the ability to have the advantages of both materials, while limiting the disadvantages of either. However, both the non-resorbable xenografts and the resorbable allografts need to be purchased separately since they may not be combined together for safety reasons as they originate from different species. This results in added costs for the treating clinician. This may be overcome by the production of non-resorbable allografts that have been processed at high temperatures. The non-resorbable allografts may then be combined with standard resorbable allografts, which provide the same benefits in one product without requiring any xenograft material. The result is improved graft handling, cost, and help ensure that clinicians use the most appropriate biomaterials.

EXAMPLE 2

A commonly used procedure during implant dentistry, particularly in the esthetic zone, involves the use of an autogenous bone layer directly positioned on a buccal surface of an implant followed by an outer xenograft layer. The xenograft layer requires the use of a non-resorbable xenograft as the use of allografts, alone, may result in resorption occurring and the patient thereby losing bone volume. A problem of this technique is that xenografts are not very osteoconductive due to their lack of osteoinductive proteins that are lost during the processing. Since it is not possible to package allografts with xenografts, the clinician must purchase separate allograft and xenograft products in order to improve the osteoinductive properties of the outer "contour" layer. These products may not be pre-packaged together due to their different origins. Instead, the non-resorbable allograft disclosed herein could be combined with a highly inductive demineralized allograft packaged together in various ratios and used to further increase bone regeneration in a defect type.

EXAMPLE 3

Complex vertical and horizontal bone augmentation procedures used in dentistry are commonly performed with standard allografts. However, due to their resorbable properties, resorption and bone loss over time may occur. The non-resorbable allograft disclosed herein may be combined with a standard allograft to better maintain bone volume gains years following surgery.

It is to be understood that the various embodiments described in this specification and as illustrated in the attached drawings are simply exemplary embodiments illustrating the inventive concepts as defined in the claims. As a result, it is to be understood that the various embodiments described and illustrated may be combined from the inventive concepts defined in the appended claims.

In accordance with the provisions of the patent statutes, the present invention has been described to represent what is considered to represent the preferred embodiments. However, it should be noted that this invention can be practiced in other ways than those specifically illustrated and described without departing from the spirit or scope of this invention.

What is claimed is:

1. A method for making a non-resorbable bone allograft, the method comprising:
    excising a bone allograft from a human donor's body;
    freeze-drying the bone allograft;
    thermal processing a first set of the freeze-dried bone allograft, wherein the first set of the freeze-dried bone allograft is mineralized, and wherein the thermal processing is performed:
    (i) at a temperature about 1,200 degrees Celsius for about one hour;
    (ii) at a temperature about 900 degrees Celsius for about four hours; or
    (iii) at a temperature about 300 degrees Celsius for about twelve hours, thus forming a non-resorbable, mineralized first set of bone allograft; and
    preserving and sterilizing the non-resorbable, mineralized first set of bone allograft.

2. The method of claim 1, further comprising, prior to preserving and sterilizing the non-resorbable, mineralized first set of bone allograft,
    demineralizing a second set of the freeze-dried bone allograft, wherein the second set of the freeze-dried bone allograft is not thermally processed, thus providing a demineralized second set of bone allograft; and
    combining the demineralized second set of bone allograft with the non-resorbable, mineralized first set of bone allograft.

3. The method of claim 2, wherein the second set of the freeze-dried bone allograft is demineralized with hydrochloric acid until a calcium content is reduced to less than 2%.

4. The method of claim 2, further comprising combining a third set of the freeze-dried bone allograft with the non-resorbable, mineralized first set of bone allograft and the demineralized second set of bone allograft.

5. The method of claim 1, wherein the freeze-drying of the bone allograft comprises placing the bone allograft into a condenser, wherein the temperature of the condenser is between about −60 degrees and −70 degrees Celsius.

6. The method of claim 1, further comprising, prior to thermal processing the first set of the freeze-dried bone allograft, rehydrating the freeze-dried bone allograft.

7. The method of claim 1, wherein the preserving and sterilizing of the non-resorbable, mineralized first set of bone allograft is by irradiation and/or immersion with ethylene oxide.

8. The method of claim 1, further comprising combining the non-resorbable, mineralized first set of bone allograft with a demineralized resorbable bone allograft.

9. The method of claim 1, further comprising, prior to preserving and sterilizing the non-resorbable, mineralized first set of bone allograft,
    demineralizing a second set of the freeze-dried bone allograft, wherein the second set of the freeze-dried bone allograft is not thermally processed, thus providing a demineralized second set of bone allograft;

providing a third set of the freeze-dried bone allograft, wherein the third set of the freeze-dried bone allograft is mineralized and not thermally processed; and
combining the non-resorbable, mineralized first set of bone allograft, the demineralized second set of bone allograft, and the third set of the freeze-dried bone allograft.

\* \* \* \* \*